(12) United States Patent
Nam et al.

(10) Patent No.: US 11,982,618 B2
(45) Date of Patent: May 14, 2024

(54) METHOD OF CALIBRATING OPTICAL SENSOR, OPTICAL SENSOR, AND APPARATUS FOR ESTIMATING BIO-INFORMATION

(71) Applicant: SAMSUNG ELECTRONICS CO., LTD., Suwon-si (KR)

(72) Inventors: Sung Hyun Nam, Yongin-si (KR); Hyeong Seok Jang, Seoul (KR); Jin Young Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 638 days.

(21) Appl. No.: 17/084,296

(22) Filed: Oct. 29, 2020

(65) Prior Publication Data

US 2021/0356322 A1 Nov. 18, 2021

(30) Foreign Application Priority Data

May 18, 2020 (KR) .................. 10-2020-0058975

(51) Int. Cl.
*G01N 21/47* (2006.01)
*A61B 5/145* (2006.01)
(Continued)

(52) U.S. Cl.
CPC ..... *G01N 21/4785* (2013.01); *A61B 5/14532* (2013.01); *A61B 5/14546* (2013.01);
(Continued)

(58) Field of Classification Search
CPC .. G01N 21/4785; G01N 21/274; G01N 21/31; G01N 21/474; G01N 21/49; G01N 2201/12707; A61B 5/14532; A61B 5/14546; A61B 5/1455; A61B 5/1495; A61B 5/681; A61B 5/6898; A61B 5/0059;
(Continued)

(56) References Cited

U.S. PATENT DOCUMENTS 4,655,225 A 4/1987 Dahne et al.
5,835,230 A 11/1998 McAndrew et al.
(Continued)

FOREIGN PATENT DOCUMENTS

JP 2011-185634 A 9/2011
KR 10-2017-0143351 A 12/2017
WO 2019/115690 A1 6/2019

OTHER PUBLICATIONS

Communication dated Oct. 14, 2021 issued by the European Patent Office in European Application No. 21172274.9.

*Primary Examiner* — Tarifur R Chowdhury
*Assistant Examiner* — Carlos Perez-Guzman
(74) *Attorney, Agent, or Firm* — Sughrue Mion, PLLC

(57) ABSTRACT

A method of calibrating an optical sensor may include acquiring a first characteristic for an external light source through a detector of an optical sensor while an internal light source of the optical sensor is turned off; driving the internal light source; acquiring a second characteristic for the internal light source and the external light source through the detector, based on driving the internal light source; and acquiring a reference characteristic of the internal light source, for calculation of an absorbance of an object, based on the first characteristic and the second characteristic.

8 Claims, 15 Drawing Sheets

(51) Int. Cl.
*A61B 5/1455* (2006.01)
*A61B 5/1495* (2006.01)
*G01J 3/02* (2006.01)
*G01J 3/10* (2006.01)

(52) U.S. Cl.
CPC .......... *A61B 5/1455* (2013.01); *A61B 5/1495* (2013.01); *G01J 3/021* (2013.01); *G01J 3/0297* (2013.01); *G01J 3/10* (2013.01); *A61B 2562/0238* (2013.01)

(58) Field of Classification Search
CPC ................ A61B 5/0022; A61B 5/6802; A61B 2562/0238; A61B 2560/0223; G01J 3/021; G01J 3/0297; G01J 3/10
See application file for complete search history.

(56) References Cited

U.S. PATENT DOCUMENTS

| | | |
|---|---|---|
| 6,469,303 B1 | 10/2002 | Sun et al. |
| 8,848,187 B2 | 9/2014 | Uematsu et al. |
| 9,400,213 B2 | 7/2016 | Uematsu et al. |
| 10,132,748 B2 | 11/2018 | Helfmann et al. |
| 10,241,033 B2 | 3/2019 | Uematsu et al. |
| 2004/0133086 A1 | 7/2004 | Ciurczak et al. |
| 2007/0047600 A1 | 3/2007 | Luo et al. |
| 2007/0123759 A1 | 5/2007 | Grata et al. |
| 2015/0219496 A1 | 8/2015 | Nakamura |
| 2015/0247795 A1 | 9/2015 | Hruska et al. |
| 2017/0143209 A1* | 5/2017 | Lee ..................... A61B 5/1455 |
| 2018/0088044 A1 | 3/2018 | Wijbrans et al. |
| 2018/0313690 A1* | 11/2018 | Hruska ................. G01J 3/0297 |
| 2019/0086263 A1 | 3/2019 | Gatto et al. |
| 2019/0113387 A1 | 4/2019 | Lee et al. |
| 2019/0204220 A1 | 7/2019 | Jang et al. |
| 2020/0281477 A1* | 9/2020 | Islam ................... G01N 33/025 |

* cited by examiner

METHOD OF CALIBRATING OPTICAL SENSOR, OPTICAL SENSOR, AND APPARATUS FOR ESTIMATING BIO-INFORMATION

CROSS-REFERENCE TO RELATED APPLICATION(S)

This application claims priority to Korean Patent Application No. 10-2020-0058975, filed on May 18, 2020, in the Korean Intellectual Property Office, the disclosure of which is incorporated by reference herein in its entirety.

BACKGROUND

1. Field

Example embodiments of disclosure relate to a method of calibrating an optical sensor, the optical sensor, and a technology for estimating bio-information using the optical sensor.

2. Description of Related Art

Recently, a technology for non-invasive analysis of various components of a subject, particularly, human tissue, using an optical sensor has been developed. In general, an optical sensor uses a separate scattering reflector to measure a spectrum of a light source before measuring spectrum of human skin, and the optical sensor is calibrated using the measured spectrum. However, since the spectrum or intensity may change due to heat generation of the light source, temperature change caused by skin contact, change in ambient temperature, and deterioration of performance of the light source, the accuracy of bio-information estimation may be reduced. In addition, in the case of using a plurality of light sources, it is not easy to calibrate the light sources due to different thermal characteristics of each light source.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, a method of calibrating an optical sensor may include acquiring a first characteristic for an external light source through a detector of an optical sensor while an internal light source of the optical sensor is turned off; driving the internal light source; acquiring a second characteristic for the internal light source and the external light source through the detector, based on driving the internal light source; and acquiring a reference characteristic of the internal light source, for calculation of an absorbance of an object, based on the first characteristic and the second characteristic.

The reference characteristic may include at least one of an intensity and a spectral characteristic of light that is emitted from the internal light source and that is reflected on an inner reflective surface of the optical sensor.

The acquiring of the reference characteristic may include acquiring the reference characteristic by subtracting the first characteristic from the second characteristic.

The driving of the internal light source may include modulating at least one of an amplitude and a phase of the internal light source, and wherein the acquiring of the reference characteristic comprises acquiring the reference characteristic using a lock-in detection technique.

The method may include comparing the reference characteristic and an initial characteristic; and determining whether to perform re-measurement, based on comparing the reference characteristic and the initial characteristic.

The method may include providing guidance to perform the re-measurement, based on determining that the re-measurement is to be performed.

The method may include performing an initial calibration; and acquiring the initial characteristic, based on performing the initial calibration.

The performing of the initial calibration may include driving the internal light source in a shielded environment, and wherein the acquiring the initial characteristic comprises acquiring the initial characteristic by detecting light, reflected by an inner reflective surface of the optical sensor, through the detector.

The performing of the initial calibration may include acquiring a third characteristic by detecting light, reflected by an outer reflective surface, through the detector in the shielded environment, and acquiring a spectral transmission constant for calculation of the absorbance of the object based on the initial characteristic and the third characteristic.

The acquiring of the spectral transmission constant may include normalizing the third characteristic and the initial characteristic, and acquiring a ratio of normalized values as the spectral transmission constant.

According to an aspect of an example embodiment, a method of calibrating an optical sensor may include driving an internal light source of an optical sensor; acquiring a characteristic for the internal light source and an external light source through a detector of the optical sensor, based on driving the internal light source; and acquiring a reference characteristic of the internal light source, for calculation of an absorbance of an object, based on the acquired characteristic.

The driving of the internal light source may include modulating at least one of an amplitude and a phase of the internal light source, and wherein the acquiring of the reference characteristic comprises acquiring the reference characteristic using a lock-in detection technique.

According to an aspect of an example embodiment, a method of calibrating an optical sensor may include driving an internal light source based on an object being in contact with an optical sensor; modulating a degree of reflection of an inner reflective surface of the optical sensor by applying a voltage to a reflective surface modulator of the optical sensor, based on driving the internal light source; detecting, through a detector of the optical sensor, light of the internal light source which is reflected by the object and the inner reflective surface, based on modulating the degree of reflection of the inner reflective surface; and acquiring a reference characteristic of the internal light source, for calculation of an absorbance of the object, using a lock-in detection technique based on the detected light.

The method may include comparing the reference characteristic and an initial characteristic of the internal light source; determining whether to perform re-measurement, based on comparing the reference characteristic and the initial characteristic; and providing guidance to perform re-measurement based on determining that the re-measurement is to be performed.

The method may include performing an initial calibration; and acquiring the reference characteristic, based on performing the initial calibration.

According to an aspect of an example embodiment, an optical sensor may include an internal light source disposed on a substrate; a detector disposed on the substrate, and that is spaced apart from the internal light source; a partition wall disposed between the internal light source and the detector, and that is configured to block light of the internal light source; and an inner reflective surface configured to reflect light of the internal light source toward the detector.

The optical sensor may include a cover surface made of a transparent material.

The optical sensor may include a modulator configured to modulate at least one of an amplitude and a phase of the internal light source.

The optical sensor may include a reflective surface modulator configured to modulate a degree of reflection of the inner reflective surface based on an applied voltage.

According to an aspect of an example embodiment, an apparatus for estimating bio-information may include an optical sensor including an internal light source configured to emit light towards an object, an inner reflective surface configured to reflect a part of the light, emitted from the internal light source, toward a detector, and the detector configured to detect the light; and a processor configured to acquire a reference characteristic of the internal light source based on performing calibration of the optical sensor; and estimate bio-information based on the reference characteristic and the light scattered or reflected from the object.

The processor may be configured to acquire a first characteristic based on light of an external light source while the internal light source is turned off, based on a request for the performing of the calibration; acquire a second characteristic based on light of the internal light source and the light of the external light source, based on driving the internal light source; and acquire the reference characteristic based on the first characteristic and the second characteristic.

The processor may be configured to acquire the reference characteristic by subtracting the first characteristic from the second characteristic.

The processor may be configured to modulate at least one of an amplitude and a phase of the internal light source based on driving the internal light source; and acquire the reference characteristic using a lock-in detection technique based on the first characteristic and the second characteristic.

The processor may be configured to compare an initial characteristic for the internal light source and a reference characteristic acquired based on performing the calibration; and determine whether to perform re-calibration based on comparing the initial characteristic and the reference characteristic.

The processor may be configured to perform an initial calibration by driving the internal light source in a shielded environment; and acquire, based on performing the initial calibration, the initial characteristic for the internal light source and a spectral transmission constant based on light reflected by the inner reflective surface and light reflected by an outer reflective surface.

The processor may be configured to acquire a spectral absorbance based on light detected from the object, the spectral transmission constant, and the reference characteristic; and estimate the bio-information using the acquired spectral absorbance and a bio-information estimation model.

The bio-information may include one or more of antioxidant components, blood sugar, triglycerides, cholesterols, proteins, carotenoids, lactates, and uric acid.

The optical sensor may include a reflective surface modulator configured to modulate a degree of reflection of the inner reflective surface based on an applied voltage.

The processor may be configured to modulate the degree of reflection of the inner reflective surface by applying a voltage to the reflective surface modulator based on the optical sensor being in contact with the object; and acquire the reference characteristic through a lock-in detection technique based on light reflected by the inner reflective surface and the object.

The processor may be configured to continuously perform the calibration and estimation of the bio-information based on the object being in contact with the optical sensor.

Other features and aspects will be apparent from the following detailed description, the drawings, and the claims.

BRIEF DESCRIPTION OF THE DRAWINGS

The above and/or other aspects will be more apparent by describing certain example embodiments, with reference to the accompanying drawings, in which.

Figure 1:
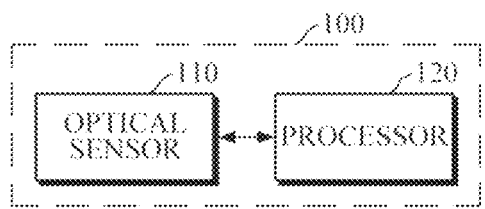
FIG. 1 is a block diagram illustrating an apparatus for estimating bio-information according to an example embodiment.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

DETAILED DESCRIPTION

Details of example embodiments are provided in the following detailed description with reference to the accompanying drawings. The disclosure may be understood more readily by reference to the following detailed description of example embodiments and the accompanying drawings. The disclosure may, however, be embodied in many different forms and should not be construed as being limited to the embodiments set forth herein. Rather, these embodiments are provided so that the disclosure will be thorough and complete and will fully convey the inventive concept to those skilled in the art. Like reference numerals refer to like elements throughout the specification.

It will be understood that, although the terms "first," "second," etc. may be used herein to describe various elements, these elements should not be limited by these terms. These terms are used to distinguish one element from another. Also, the singular forms of terms are intended to include the plural forms of the terms as well, unless the context clearly indicates otherwise. In the specification, unless explicitly described to the contrary, the word "comprise," and variations such as "comprises" or "comprising," will be understood to imply the inclusion of stated elements but not the exclusion of any other elements. Terms such as "unit" and "module" denote units that process at least one function or operation, and that may be implemented by using hardware, software, or a combination of hardware and software.

Hereinafter, example embodiments of the biometric information estimation apparatus, the optical sensor, and the method for calibrating the optical sensor will be described in detail with reference to the drawings.

FIG. 1 is a block diagram illustrating an apparatus for estimating bio-information according to an example embodiment. FIGS. 2 to 7 are diagrams for describing an optical sensor and calibration of the optical sensor according to example embodiments.

Referring to FIG. 1, the apparatus 100 for estimating bio-information includes an optical sensor 110 and a processor 120.

The optical sensor 110 may emit light to an object and detect a light signal scattered or reflected from the object.

Figure 2:
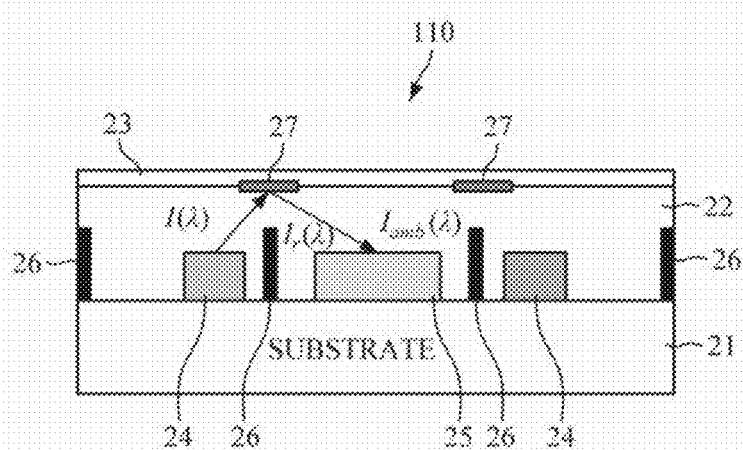
FIG. 2 is a diagram illustrating an optical sensor according to an example embodiment.

FIG. 2 is a diagram illustrating an optical sensor according to an example embodiment.

Referring to FIGS. 1 and 2, the optical sensor 110 includes an internal light source 24 and a detector 25. The internal light source 24 and the detector 25 may be disposed on a substrate 21 to be spaced apart from each other. The internal light source 24 may include a light emitting diode (LED), a laser diode, a phosphor, and the like, but is not limited thereto. The detector 25 may include a photodiode, a photo transistor, an image sensor, a spectrometer, and the like, but is not limited thereto.

The internal light source 24 and the detector 25 may be configured as one or a plurality of arrays and be arranged in various forms, such as concentric circles, rectangles, triangles, and linear shapes. For example, a plurality of LED arrays may be arranged around the photodiode in the form of a concentric circle, a rectangle, or the like, or conversely, a plurality of photodiodes may be arranged around one light source in the form of a concentric circle, a rectangle, or the like. The number and arrangement form of the internal light sources 24 and the detectors 25 are not particularly limited and may be variously modified according to the type of bio-information to be analyzed or the computing performance of the apparatus 100 for estimating bio-information.

The internal light source 24 and the detector 25 may be formed on the substrate 21 by wire bonding or flip-chip bonding, or may be patterned on the substrate 21 by microfabrication techniques.

The optical sensor 110 may include a partition wall 26 disposed between the internal light source 24 and the detector 25 to block the light emitted from the internal light source 24 from directly traveling to the detector 25.

Alternatively, the optical sensor 110 may further include an inner reflective surface 27 that reflects a part of the light emitted toward the object from the internal light source 24 to direct the light to the detector 25. The inner reflective surface 27 may be disposed on the partition wall 26 between the internal light source 24 and the detector 25 as illustrated in the drawings. The inner reflective surface 27 may be formed as an object that reflects light, such as a mirror or a metal object, or a material that reflects light may be applied to the object.

The optical sensor 110 may have a cover surface 23 that contacts the object and the inner reflective surface 27 may be disposed on the cover surface 23. In this case, the cover surface 23 may be made of a transparent material, such as glass, so that light emitted from the internal light source 24 and the light reflected by the object can be transmitted. A space 22 between the substrate 21 and the cover surface 23 may be molded.

The processor 120 may be electrically connected to the optical sensor 110. The processor 120 may control the optical sensor 110 in response to a request for estimating bio-information and estimate bio-information based on characteristics of a signal received from the optical sensor 110. In this case, the bio-information may include one or more of antioxidant components, blood sugar, triglycerides, cholesterols, proteins, carotenoids, lactates, and uric acid. However, the bio-information is not limited thereto.

In order to increase the accuracy of bio-information estimation, the processor 120 may perform initial calibration at the time of manufacture of the apparatus 100 for estimating bio-information or at the time of the user's initial use of the apparatus 100.

Figure 3:
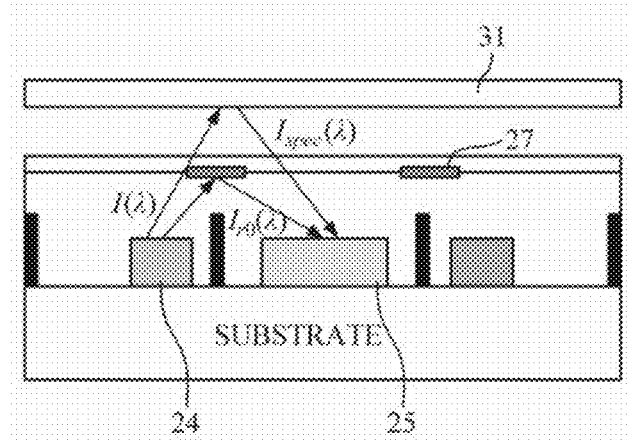
FIG. 3 is a diagram for describing initial calibration.

FIG. 3 is a diagram for describing initial calibration.

Referring to FIG. 3, the processor 120 may first drive the internal light source 24 in a shielded environment to emit light having an optical characteristic of $I(\lambda)$. When the light emitted by the internal light source 24 is reflected by the inner reflective surface 27, the detector 25 may detect the light reflected by the inner reflective surface 27 and the processor 120 may store an optical characteristic of $I_{r0}(\lambda)$ detected by the detector 25 as an initial characteristic for the internal light source 24. In this case, the optical characteristic detected through the detector 25 may be a wavelength, a light intensity, or a spectral characteristic depending on the configuration of the detector 25, and may be described as light intensity, absorbance, or the like, for convenience of description.

Then, the processor 120 may drive the internal light source 24 in a shielded environment to emit light toward an outer reflective surface 31 and may acquire a spectral transmission constant based on the optical characteristic detected by the detector 25. In this case, the detected optical characteristic may include the light reflected by the outer reflective surface 31 and the inner reflective surface 27.

For example, the spectral transmission constant may be obtained by referring to Equation 1 below.

$$I_1(\lambda) = I_{spec}(\lambda) + I_{r0}(\lambda)$$

$$I_{spec}(\lambda) = I_1(\lambda) - I_{r0}(\lambda)$$

$$k(\lambda) = I_{spec}^{norm}(\lambda) / I_{r0}^{norm}(\lambda) \qquad \text{Equation (1)}$$

The processor 120 may acquire an optical characteristic $I_{spec}(\lambda)$ of the light reflected by the outer reflective surface 31 by subtracting an initial optical characteristic $I_{r0}(\lambda)$ from an optical characteristic $I_1(\lambda)$ of the light reflected by the outer reflective surface 31 and the inner reflective surface 27. In this case, the optical characteristic $I_{spec}(\lambda)$ of the light reflected by the outer reflective surface 31 may converge to a value similar to the optical characteristic $I_0(\lambda)$ of the light emitted by the internal light source 24 if the optical characteristic of the light reflected by the inner reflective surface, i.e., the initial optical characteristic $I_{r0}(\lambda)$ is very small.

The processor 120 may acquire a ratio between the acquired optical characteristic $I_{spec}(\lambda)$ of the light reflected by the outer reflective surface and the initial optical characteristic $I_{r0}(\lambda)$ of the light reflected by the inner reflective surface 27 as the spectral transmission constant. In this case, the optical characteristics $I_{spec}(\lambda)$ and $I_{r0}(\lambda)$ of the light reflected respectively by the outer reflective surface and the inner reflective surface may be normalized and the spectral transmission constant may be acquired using normalized optical characteristics $I_{spec}^{norm}(\lambda)$ and $I_{r0}^{norm}(\lambda)$. At this time, normalization may be performed such that the optical characteristic, for example, light intensity, has a value in a range from 0 to 1.

The processor 120 may store the acquired initial characteristic and spectral transmission constant as initial calibration information, and utilize the stored initial calibration information when estimating biometric information.

When the optical characteristics are detected through the detector 25, the processor 120 may use the detected optical characteristic value to obtain the initial characteristic and the spectral transmission constant, but may use a value obtained by subtracting, from the optical characteristic value, an optical characteristic $I_{dark}$ that is detected through the detector 25 without driving the internal light source in a shielded environment.

The initial calibration process described above may be omitted. For example, the initial characteristic and the spectral transmission constant may be acquired using values acquired through preprocessing in other devices or similar environments.

As the bio-information estimation is repeated, the spectral characteristic or the intensity of a light signal of the optical sensor 110 may change due to changes in the measurement environment, such as heat generation of the internal light source 24, temperature change due to contact with the object, change in ambient temperature, deterioration of performance of the internal light source 24, and the like, and the change in the optical characteristic of the internal light source may reduce the accuracy of bio-information estimation.

The processor 120 may additionally perform calibration in order to correct the change in the optical characteristic due to the repeated bio-information estimation. For example, the processor 120 may perform calibration, for example, at the user's request, at a predetermined interval, or before bio-information estimation.

Alternatively, the processor 120 may perform calibration on the basis of whether the environment for bio-information estimation has changed drastically or whether the accuracy of the bio-information estimation result has been reduced. For example, the apparatus 100 for estimating bio-information may further include a temperature sensor for measuring contact temperature of the object or the heat generation of the internal light source. The processor 120 may determine that the environment has changed drastically when the temperature measured using the temperature sensor, or the like, is not within a normal range. Alternatively, the processor 120 may determine that the accuracy of the bio-information estimation is reduced when the bio-information estimation result deviates from a normal range by more than a predetermined threshold or when the number of times the bio-information estimation result deviates from the normal range is greater than a predetermined threshold. However, these are merely examples, and the conditions for determination may be set variously.

Figure 4:
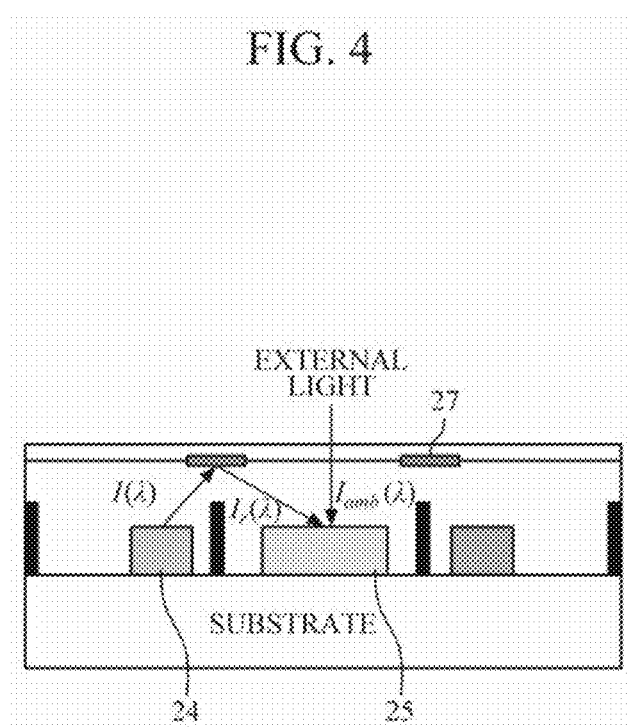
FIG. 4 is a diagram for describing an example embodiment of calibration performed at the time of bio-information estimation.

FIG. 4 is a diagram for describing an example embodiment of additional calibration performed at the time of bio-information estimation. A calibration method according to an example embodiment will be described with reference to FIG. 4.

A processor 120 may turn off an internal light source 24 of an optical sensor and control a detector 25 to acquire an optical characteristic $I_{amb}(\lambda)$ for an external light source.

Then, the processor 120 may drive the internal light source 24 and detect light from the external light source and light reflected on an inner reflective surface 27 through the detector 25. Also, the processor 120 may use the detected light to determine an optical characteristic $I_2(\lambda)=I_{amb}(\lambda)+I_r(\lambda)$ for the internal light source 24 and the external light source.

The processor 120 may acquire a reference characteristic $I_r(\lambda)$ for use in calculation of absorbance by subtracting the optical characteristic $I_{amb}(\lambda)$ for the external light source from the optical characteristic $I_2(\lambda)$ for the internal light source 24 and the external light source as shown in Equation 2 below. The processor 120 may perform preprocessing including smoothing on the acquired reference characteristic and store the preprocessed reference characteristic.

$$I_r(\lambda)=I_2(\lambda)-I_{amb}(\lambda) \quad \text{Equation (2)}$$

When the reference characteristic is acquired, the processor 120 may compare the reference characteristic and an initial characteristic acquired in the process of initial calibration and determine whether to perform re-measurement. For example, when a difference between the initial characteristic and the reference characteristic exceeds a predetermined threshold, the optical characteristic of the internal light source has changed to an extent that affects the accuracy of the bio-information estimation and guidance may be provided to a user.

When a request for estimating bio-information is received, the processor 120 may estimate bio-information using the reference characteristic acquired through calibration. In this case, the request for estimating bio-information may be received through a predetermined interval, a user's input, or an external device.

Figure 5:
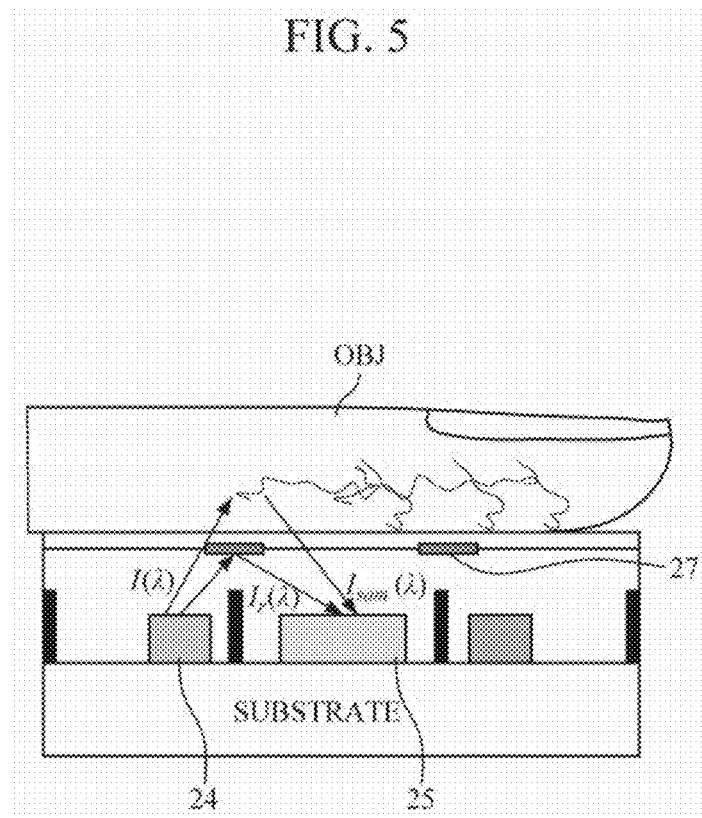
FIG. 5 is a diagram for describing bio-information estimation.

FIG. 5 is a diagram for describing bio-information estimation.

Referring to FIG. 5, when an object OBJ is in contact with an optical sensor 110, a processor 120 may drive an internal light source 24 to emit light having an optical characteristic $I(\lambda)$ to the object OBJ. A detector 25 may detect light that is emitted by the internal light source 24 and is scattered or reflected by an inner reflective surface 27, a surface of the object OBJ, or a measurement site, for example, a blood vessel, inside the object OBJ.

The processor 120 may calculate the absorbance based on the characteristics of the light detected through the detector 25, and reference characteristics and a spectral transmission constant acquired through calibration, and calculate a bio-information estimation value using the absorbance.

For example, an absorbance calculation equation based on Lambert-Beer's law is shown as Equation 3 below but is not limited thereto.

$$Y = \log_{10}\left(\text{abs}\left[\frac{I_r \times k}{I_{sam} - I_r}\right]\right) \quad \text{Equation (3)}$$

In Equation 3, Y represents an absorbance at a wavelength of $\lambda$. abs represents an absolute value, $I_r$ represents a reference characteristic, k represents a spectral transmission constant acquired through initial calibration, and $I_{sam}$ represents an optical characteristic detected by the detector 25 after emitting light to an object. The intensity of light scattered or reflected from the object may be obtained by subtracting the reference characteristic $I_r$ from the detected optical characteristic $I_{sam}$.

When the absorbance is calculated as described above, the processor 120 may estimate bio-information using the absorbance. For example, the bio-information estimation value may be acquired using a bio-information estimation model that defines a correlation between the absorbance and bio-information.

Figure 6:
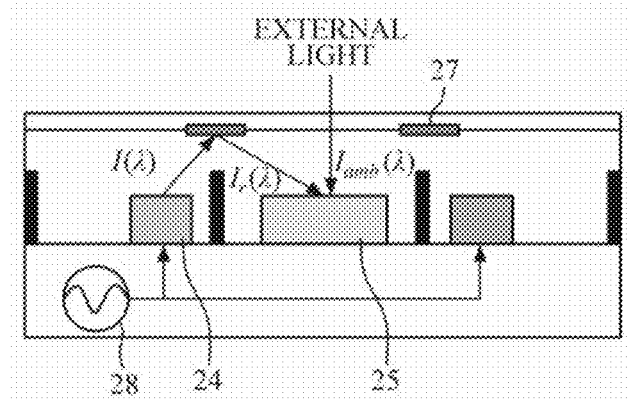
FIG. 6 is a diagram for describing an optical sensor and a calibration method according to another example embodiment.

FIG. 6 is a diagram for describing an optical sensor and a calibration method according to another example embodiment.

Referring to FIG. 6, an optical sensor 110 may further include a modulator 28 that modulates an amplitude or a phase of an internal light source 24. In an example, the processor 120 may acquire an optical characteristic $I_{amb}(\lambda)$ of an external light source while the internal light source 24 is turned off. The processor 120 may drive the internal light source 24 and control the modulator 28 to perform quadrature amplitude modulation, phase modulation, and the like, of the internal light source 24. In addition, the reference characteristic $I_r(\lambda)$ may be obtained by the lock-in detection technique using the optical characteristic $I_2^{mod}(\lambda)=I_{amb}(\lambda)+I_r^{mod}(\lambda)$ detected through the detector 25. In another example, the processor 120 may acquire characteristics of the internal light source 24 and the external light source while directly modulating the internal light source 24 under the external light source, and acquire the reference characteristic using the lock-in detection technique on the basis of the acquired optical characteristics. The lock-in detection technique is a known technique, and thus a detailed description thereof will be omitted. The processor 120 may compare the reference characteristic acquired as described above and an initial characteristic and determine whether to perform re-measurement.

Figure 7:
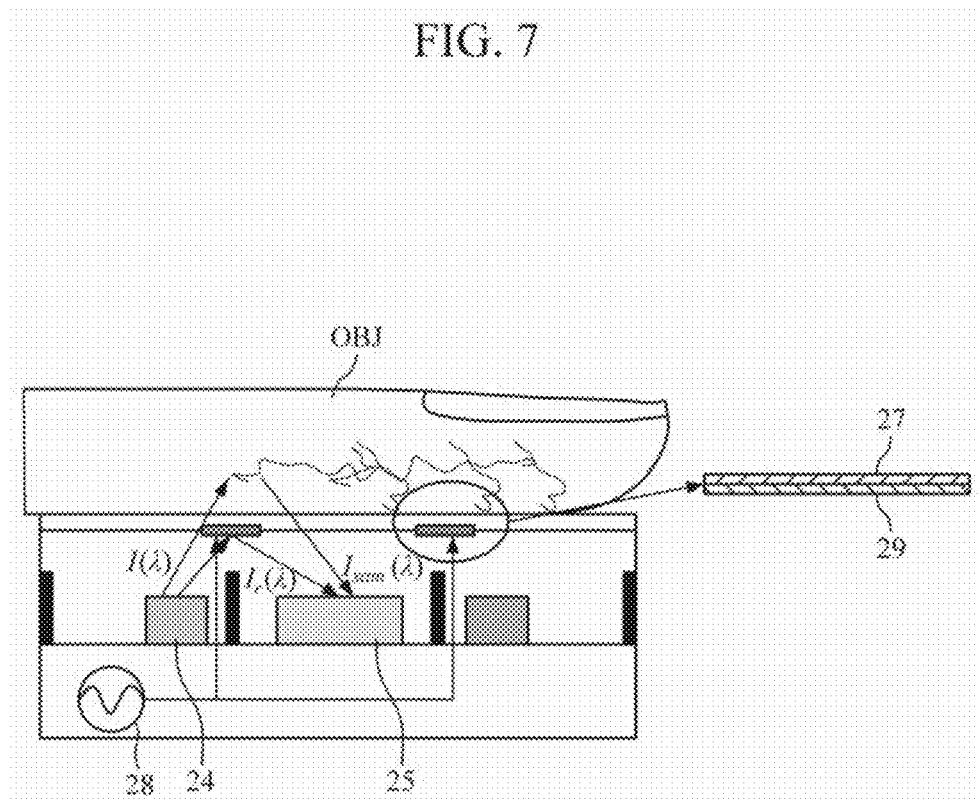
FIG. 7 is a diagram for describing an optical sensor and a calibration method according to still another example embodiment.

FIG. 7 is a diagram for describing an optical sensor and a calibration method according to still another example embodiment.

In the present example embodiment, when a user brings an object OBJ into contact with a cover surface 23 of the optical sensor 110 for bio-information estimation, calibration may be performed before estimating the bio-information. Then, once the calibration is completed, bio-information may be estimated using a signal continuously detected from the object OBJ. However, the example embodiment is not limited thereto, and it is possible to perform only the calibration process and omit the bio-information estimation process.

Referring to FIG. 7, the optical sensor 110 may further include a reflective surface modulator 29 that modulates a degree of reflection of an inner reflective surface 27. The reflective surface modulator 29 may be attached to the inner reflective surface 27 as shown in the drawings, or be integrally formed with the inner reflective surface 27. The reflective surface modulator 29 may be a liquid crystal light modulator.

The processor 120 may modulate a signal reflected by the inner reflective surface 27 by applying a voltage to the reflective surface modulator 29 through the modulator 28, and acquire a reference characteristic through a lock-in detection technique using the signal detected by a detector 25. The processor 120 may compare the reference characteristic acquired as described above and an initial characteristic and determine whether to perform re-measurement.

Figure 8:
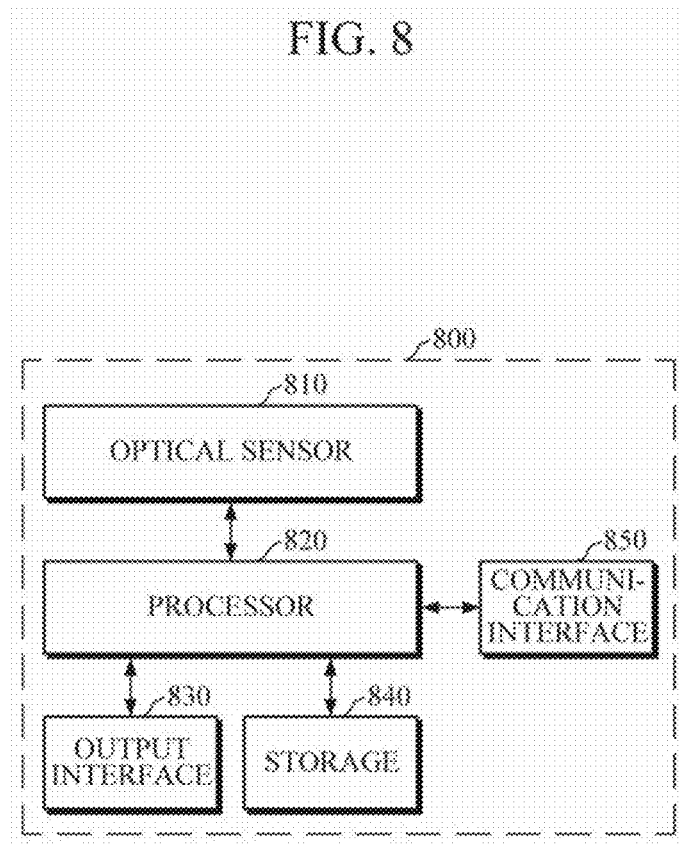
FIG. 8 is a block diagram illustrating an apparatus for estimating bio-information according to another example embodiment.

FIG. 8 is a block diagram illustrating an apparatus for estimating bio-information according to another example embodiment.

Referring to FIG. 8, an apparatus 800 for estimating bio-information may include an optical sensor 810, a processor 820, an output interface 830, a storage 840, and a communication interface 850. The configurations of the optical sensor 810 and the processor 820 have been described above, and thus detailed descriptions thereof will not be reiterated.

The output interface 830 may output a processing result of the processor 820 to a user. For example, a bio-information estimate may be provided to the user using a visual output module, such as a display, a sound output module, such as a speaker, or a haptic module that provides information through, for example, vibration or tactile sensation. In addition, the processor 820 may monitor a user's health condition on the basis of a bio-information estimation result, and the output interface 830 may output warning when a risk of the health condition is expected.

The storage 840 may store a variety of reference information for bio-information estimation or a processing result of the processor 840. For example, the reference information may include information regarding driving conditions for a light source, light source modulation, modulation of an inner reflective surface, a bio-information estimation model, and the like. Also, the reference information may include user characteristic information, such as the user's age, sex, health condition, and the like. However, the device is not limited thereto.

The storage 840 may include at least one type of storage medium of a flash memory type, a hard disk type, a multimedia card micro type, a card type memory (for example, secure digital (SD) or extreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk, but is not limited thereto.

The communication interface 850 may communicate with an external device to transmit and receive data related to bio-information estimation. In this case, the external device may include a user's portable device, such as a smartphone, a tablet personal computer (PC), a desktop computer, a notebook computer, or the like, and a device of a professional medical institution. The communication interface 850 may use Bluetooth communication, Bluetooth low energy (BLE) communication, near field communication (NFC), wireless local access network (WLAN) communication, Zigbee communication, infrared data association (IrDA) communication, wireless fidelity (Wi-Fi) direct (WFD) communication, ultra wideband (UWB) communication, Ant+ communication, Wi-Fi communication, and 3G, 4G, and 5G communication technologies. However, the communication technologies for use are not limited thereto.

FIGS. 9 to 13 are flowcharts illustrating a method of calibrating an optical sensor according to example embodiments. The method shown in FIGS. 9 to 13 may be performed by the above-described apparatuses 100 or 800 for estimating bio-information. The bio-information estimation has been described above in detail, and thus will be briefly described below to prevent redundancy.

Figure 9:
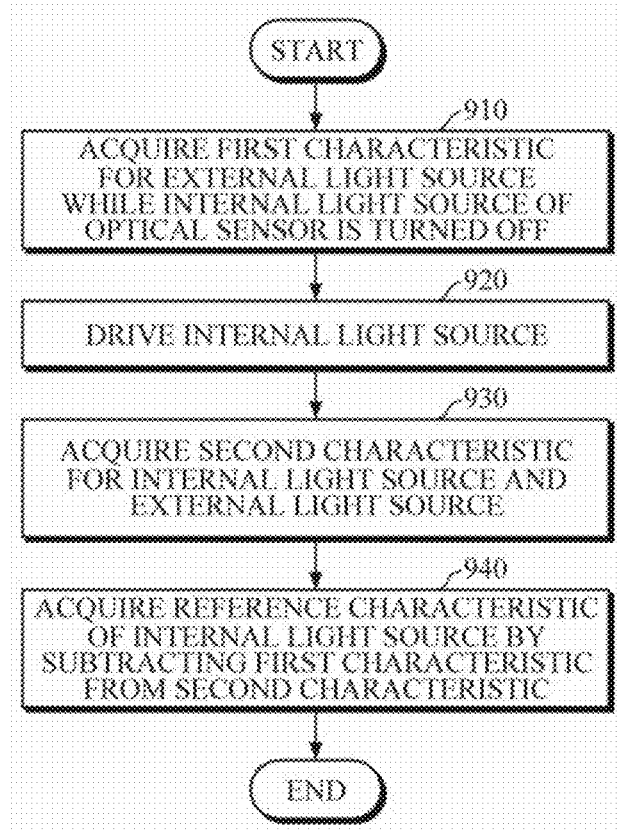
FIGS. 9 to 13 are flowcharts illustrating a method of calibrating an optical sensor according to example embodiments.

An example embodiment of a calibration method will be described with reference to FIG. 9.

First, the apparatus 100 or 800 for estimating bio-information may acquire a first characteristic for the external light source while the internal light source of the optical sensor is turned off (operation 910).

Then, the internal light source may be driven (operation 920), and a second characteristic for the internal light source and the external light source may be acquired (operation 930). At this time, the detector of the optical sensor may detect light that is emitted by the internal light source and is reflected by the inner reflective surface and light entering from the outside, and acquire the second characteristic on the basis of the detected light.

Then, a reference characteristic to be used in calculation of an absorbance may be acquired by subtracting the first characteristic from the second characteristic (operation 940). In this case, the reference characteristic may be a characteristic of the light reflected by the inner reflective surface.

Figure 10:
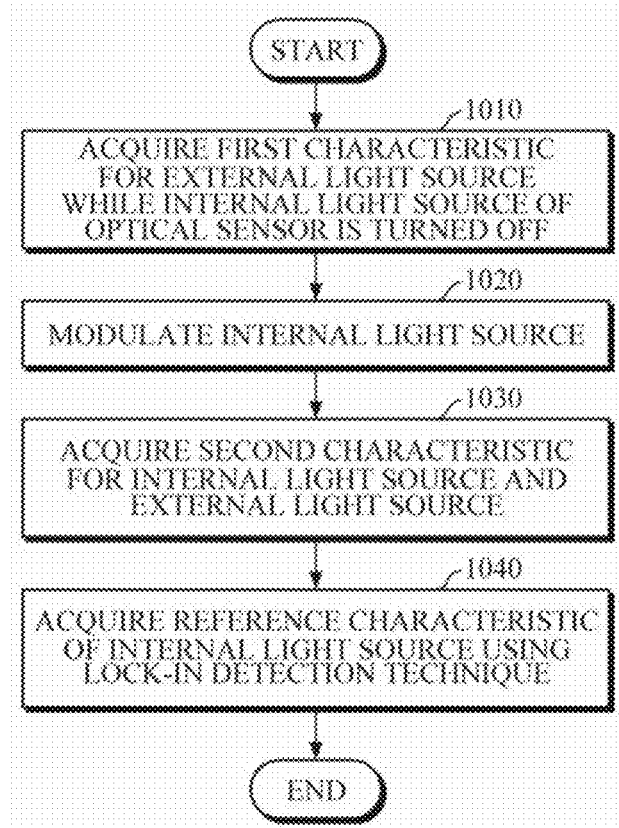

Another example embodiment of the calibration method will be described with reference to FIG. 10.

First, the apparatus 100 or 800 for estimating bio-information may acquire a first characteristic for the external light source while the internal light source of the optical sensor is turned off (operation 1010).

Then, a phase or an amplitude of the internal light source may be modulated (operation 1020), and a second characteristic for the internal light source and the external light source may be acquired (operation 1030).

Then, a reference characteristic to be used in calculation of an absorbance may be acquired using a lock-in detection technique (operation 1040).

Figure 11:
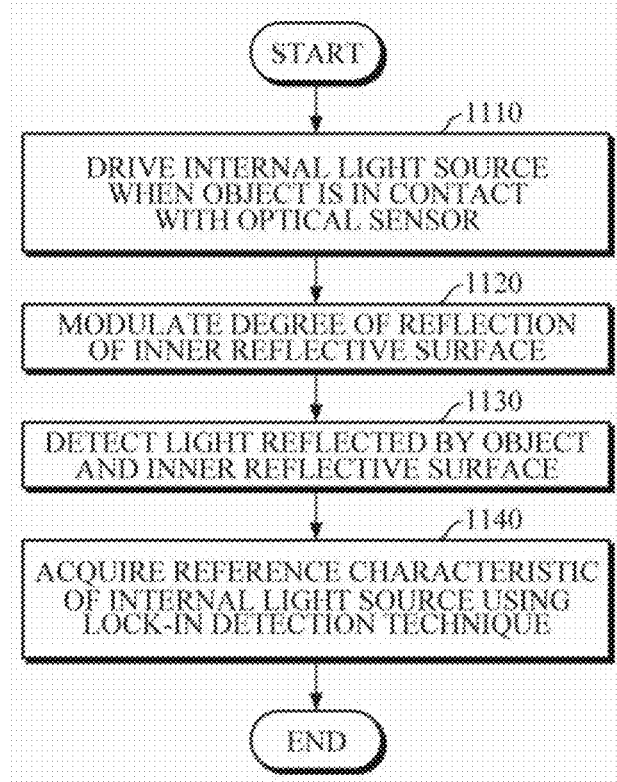

Another example embodiment of the calibration method will be described with reference to FIG. 11.

First, the apparatus 100 or 800 for estimating bio-information may drive the internal light source when an object is in contact with the optical sensor (operation 1110), and modulate a degree of reflection of the inner reflective surface by applying a voltage to the inner reflective surface (operation 1120).

Then, the light reflected by the object and the inner reflective surface may be detected (operation 1130), and the reference characteristic to be used in calculation of an absorbance may be acquired using a lock-in detection technique (operation 1140).

Another example embodiment of the calibration method will be described with reference to FIGS. 12 and 13.

First, an initial characteristic of the internal light source of the optical sensor may be acquired by performing a first calibration (operation 1210). The first calibration may be performed at the time of manufacture of the apparatus 100 or 800 or at the time of the user's initial use of the apparatus 100 or 800.

Figure 13:
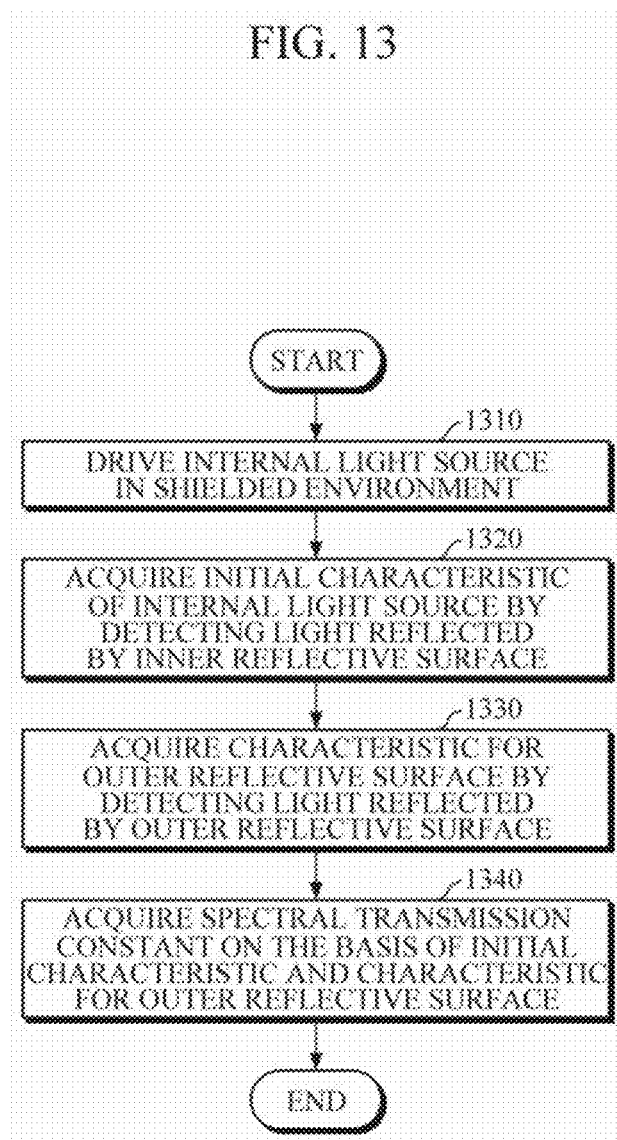

FIG. 13 illustrates an example embodiment of operation 1210 of performing the first calibration. Referring to FIG. 13, the apparatus 100 or 800 for estimating bio-information may drive the internal light source in a shielded environment (operation 1310), and acquire the initial characteristic for the internal light source by detecting light reflected by the inner reflective surface (operation 1320). Then, light may be emitted to the outer reflective surface through the internal light source and an optical characteristic for the outer reflective surface may be acquired (operation 1330). Then, a spectral transmission constant may be acquired on the basis of the initial characteristic and the characteristic for the outer reflective surface (operation 1340).

Figure 12:
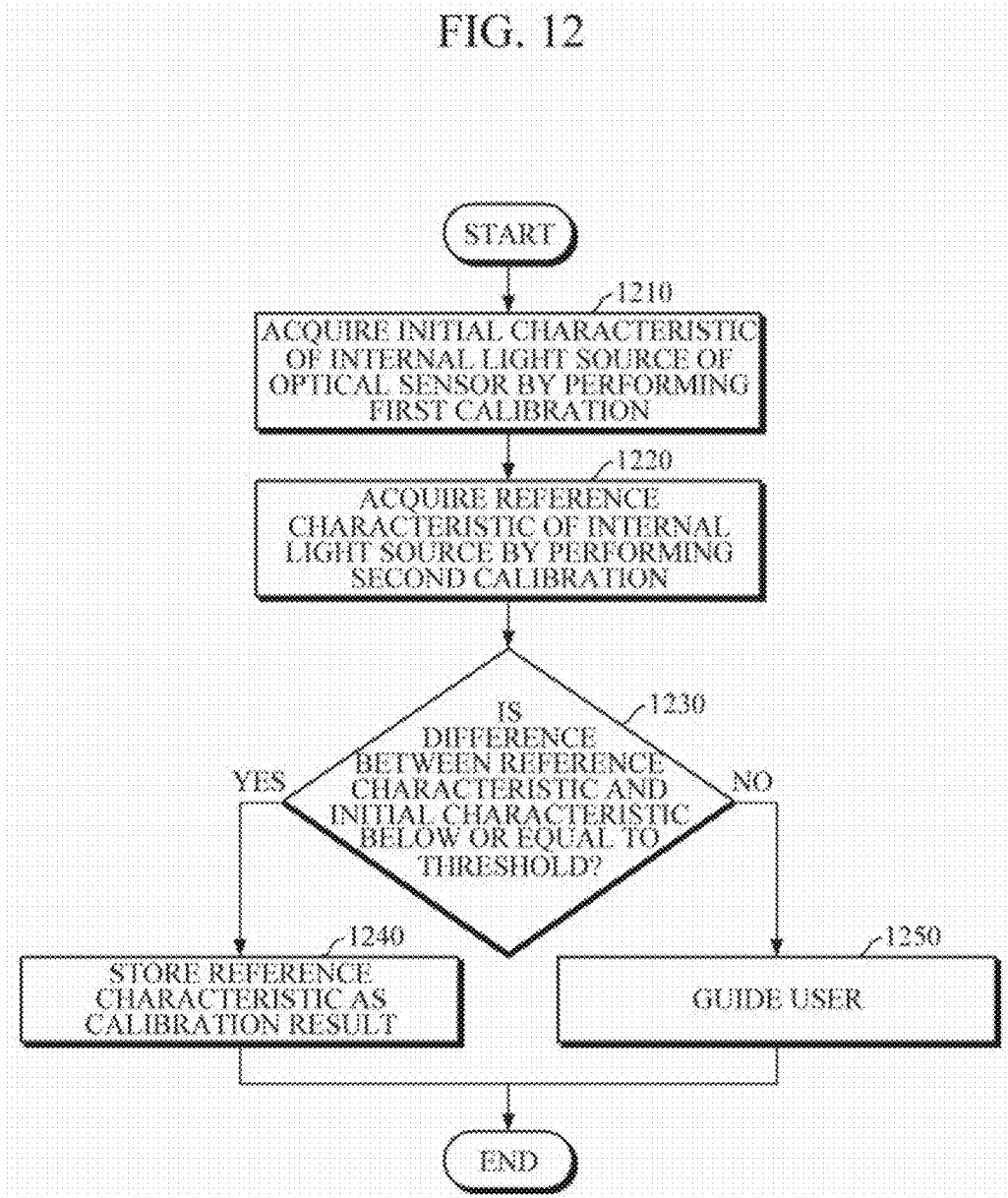

Referring to FIG. 12, the apparatus 100 or 800 for estimating bio-information may perform a second calibration to acquire a reference characteristic for the internal light source (operation 1220). The second calibration has been described with reference to FIGS. 3 to 7, and hence a detailed description thereof will be omitted below.

Then, the reference characteristic acquired in operation 1220 and the initial characteristic acquired in operation 1210 may be compared with each other (operation 1230). When a comparison result is below or equal to a threshold (operation 1230—YES), the acquired reference characteristic may be stored as a calibration result for bio-information estimation (operation 1240), and when the comparison result exceeds the threshold (operation 1230—NO), the user may be guided for re-measurement (operation 1250).

Figure 14:
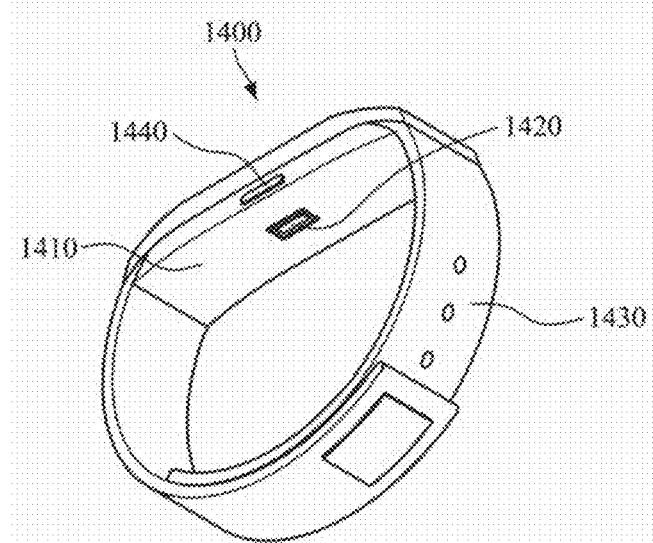
FIG. 14 is a diagram illustrating a wearable device according to an example embodiment.

FIG. 14 is a diagram illustrating a wearable device according to an example embodiment. The above-described example embodiments of the apparatuses 100 and 800 for estimating bio-information may be mounted in a smart watch or a smart band type wearable device that is worn on a wrist. However, the device is not limited thereto.

Referring to FIG. 14, a wearable device 1400 may include a main body 1410 and a strap 1430.

The main body 1410 may be formed to have various shapes. The main body 1410 may include various modules to perform a function related to bio-information estimation as well as other various functions (e.g., a watch function and an alarm function). A battery may be embedded in the main body 1410 or the strap to supply power to various modules of the wearable device 1400.

The strap 1430 may be connected to the main body 1410. The strap 1430 may be flexible, so as to be bent around a user's wrist. The strap 1430 may be bent in a manner that allows the strap 1430 to be detached from the user's wrist or may be formed as a band that is not detachable. Air may be injected into the strap 1430 or an airbag may be included in the strap 1430, so that the strap 1430 may have elasticity according to a change in pressure applied to the wrist, and the change in pressure of the wrist may be transmitted to the main body 1410.

The main body 1410 may include an optical sensor 1420. The optical sensor 1420 may be mounted on one surface of the main body 1410, which comes into contact with a user's wrist when the main body 1410 is worn on the user's wrist.

In addition, a processor may be mounted inside the main body 1410, and the processor may be electrically connected to various modules of the wearable device 1400 to control the modules.

The processor may perform calibration of the optical sensor 1420, and estimate bio-information using a light signal detected from an object through the optical sensor 1420. The user may input various commands including calibration of the optical sensor 1420 and estimation of bio-information through a display, a manipulator, and/or a voice input using a microphone.

The display may be mounted on a front surface of the main body 1410. The display may be a touch panel that includes a touch screen for touch input. The display may receive a touch input from the user, transmit the received touch input to the processor, and output a processing result of the processor. For example, the display may display a bio-information estimation result and may also display additional information, such as a bio-information estimation history, a change in health condition, a warning, and the like.

The main body 1410 may include a storage which stores a processing result of the processor and various types of information. In this case, the various types of information may include information related to other functions of the wearable device 1400 in addition to information related to estimation of bio-information.

Additionally, the main body 1410 may include a manipulator 1440 which receives a user's command and transmits the received command to the processor. The manipulator 1440 may include a power button to input a command to turn on/off the wearable device 1400.

In addition, a communication interface for communication with an external device may be mounted in the main body 1410. The communication interface may output an estimation result of bio-information to the external device, for example, a portable terminal, or may transmit the bio-information estimation result to the external device so that it can be stored in a storage module of the external device. Further, the communication interface may receive information, and the like, for supporting other various functions performed in the wearable device from the external device.

Figure 15:
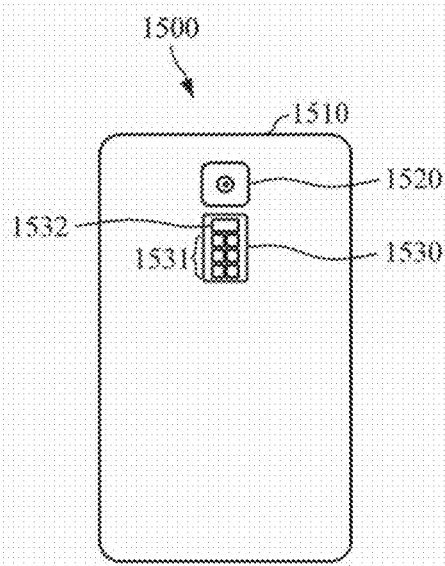
FIG. 15 is a diagram illustrating a smart device according to an example embodiment.

FIG. 15 is a diagram illustrating a smart device, to which example embodiments of the apparatus 100 or 800 for estimating bio-information are applied. In this case, the smart device may be a smartphone or a tablet PC, but is not limited thereto.

Referring to FIG. 15, the smart device 1500 may include an optical sensor 1530 mounted on one surface of a main body 1510. For example, the optical sensor 1530 may include one or more light sources 1531 and a detector 1532. The optical sensor 1530 may be mounted on a rear surface of the main body 1510 as illustrated in FIG. 15, but is not limited thereto. The optical sensor 1530 may be combined with a fingerprint sensor or a touch panel on a front surface.

A display may be mounted on the front surface of the main body 1510. The display may visually output an estimation result of bio-information and the like. The display may include a touch panel, and may receive information input through the touch panel and transmit the received information to a processor.

An image sensor 1520 may be mounted in the main body 1510. When the user brings his/her finger near the optical sensor 1530 to measure a bio-signal, the image sensor 1520 may photograph a finger and transmit the photographed image to the processor. In this case, the processor may recognize a relative position of the finger compared to a position of the optical sensor 1530 from the image of the finger and provide the relative position information of the finger to the user through the display, thereby guiding the user to bring his/her finger into accurate contact with the optical sensor 1530.

The processor may be electrically connected to various modules including the optical sensor 1530 and may control various functions including calibration of the optical sensor 1530, estimation of bio-information, and the like. In addition, the processor may output a processing result by controlling a display, and the like.

The embodiments can be implemented as computer readable code in a non-transitory computer-readable medium. Code and code segments constituting the computer program can be inferred by a skilled computer programmer in the art. The non-transitory computer-readable medium includes all types of recording media in which computer-readable data is stored. Examples of the non-transitory computer-readable medium include a ROM, a RAM, a CD-ROM, a magnetic tape, a floppy disk, and an optical data storage. Further, the recording medium may be implemented in the form of a carrier wave such as Internet transmission. In addition, the non-transitory computer-readable medium may be distributed to computer systems over a network, in which computer-readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of calibrating an optical sensor, the method comprising:
    acquiring a first characteristic for an external light source through a detector of the optical sensor while an internal light source of the optical sensor is turned off;
    driving the internal light source;
    acquiring a second characteristic for the internal light source and the external light source through the detector, based on driving the internal light source;
    acquiring a reference characteristic of the internal light source, for calculation of an absorbance of an object, based on the first characteristic and the second characteristic;
    comparing the reference characteristic and an initial characteristic; and
    determining whether to perform re-measurement, based on comparing the reference characteristic and the initial characteristic,
    wherein the acquiring the reference characteristic comprises acquiring the reference characteristic by subtracting the first characteristic from the second characteristic.

2. The method of claim 1, wherein the reference characteristic includes at least one of an intensity and a spectral characteristic of light that is emitted from the internal light source and is reflected on an inner reflective surface of the optical sensor.

3. The method of claim 1, wherein the driving the internal light source comprises modulating at least one of an amplitude and a phase of the internal light source, and
    wherein the acquiring the reference characteristic comprises acquiring the reference characteristic using a lock-in detection technique.

4. The method of claim 1, further comprising:
    providing guidance to perform the re-measurement, based on determining that the re-measurement is to be performed.

5. The method of claim 1, further comprising:
    performing an initial calibration; and
    acquiring the initial characteristic, based on performing the initial calibration.

6. The method of claim 5, wherein the performing the initial calibration comprises driving the internal light source in a shielded environment, and
    wherein the acquiring the initial characteristic comprises acquiring the initial characteristic by detecting light, reflected by an inner reflective surface of the optical sensor, through the detector.

7. The method of claim 6, wherein the performing the initial calibration comprises acquiring a third characteristic by detecting light, reflected by an outer reflective surface, through the detector in the shielded environment, and acquiring a spectral transmission constant for calculation of the absorbance of the object based on the initial characteristic and the third characteristic.

8. The method of claim 7, wherein the acquiring the spectral transmission constant comprises normalizing the third characteristic and the initial characteristic, and acquiring a ratio of normalized values as the spectral transmission constant.

* * * * *